US006090794A

United States Patent [19]

Martuza et al.

[11] Patent Number: 6,090,794
[45] Date of Patent: Jul. 18, 2000

[54] INHIBITION OF NEUROFIBROSARCOMA GROWTH AND ANGIOGENESIS

[75] Inventors: Robert L. Martuza, Lexington, Mass.; Jung Kyo Lee, Seoul, Rep. of Korea

[73] Assignee: The General Hospital Corporation, Boston, Mass.

[21] Appl. No.: 07/922,665

[22] Filed: Aug. 5, 1992

Related U.S. Application Data

[63] Continuation of application No. 07/510,251, Apr. 19, 1990, abandoned.

[51] Int. Cl.$^7$ ..................................................... A61K 31/725
[52] U.S. Cl. ............................... 514/56; 514/26; 514/54; 514/58; 514/169
[58] Field of Search ................................. 514/26, 54, 56, 514/58, 169

[56] References Cited

U.S. PATENT DOCUMENTS

| | | | |
|---|---|---|---|
| 4,596,795 | 6/1986 | Pitha | 514/58 |
| 4,710,493 | 12/1987 | Landsberger | 514/56 |
| 4,757,056 | 7/1988 | Vangorp et al. | 514/56 |
| 4,788,307 | 11/1988 | Lormeau et al. | 536/21 |
| 4,877,774 | 10/1989 | Pitha et al. | 514/58 |
| 4,994,443 | 2/1991 | Folkman et al. | 514/56 |
| 5,001,116 | 3/1991 | Folkman et al. | 514/56 |
| 5,019,562 | 5/1991 | Folkman et al. | 514/58 |
| 5,021,404 | 6/1991 | Folkman et al. | 514/56 |

FOREIGN PATENT DOCUMENTS

| | | | |
|---|---|---|---|
| 0114589 | 8/1984 | European Pat. Off. | 514/56 |
| 0140781 | 5/1985 | European Pat. Off. | 514/56 |

OTHER PUBLICATIONS

Storm et al; Cancer 45:126–129 (1980).
Sieb et al; Dtsch. Med. Wschr. 114(11):417–419 Mar. 1989.
Dillman et al; Mol. Biother. 4:117–121 (1992).
Johnson and Goldin, *Cancer Treatment Reviews* 1975, (2), 1–31.
Dorland's Pocket Medical Dictionary, 24$^{th}$ Edition, W.B. Sanders Company, 1989, pp. 529 and 532.
Folkman et al; Science 221:719–725 (1983).
Crum et al; Science 230:1375–1378 (1985).
Ziche, et al., *Int. J. Cancer*:35, 549–552 (1985).
Sakamoto, et al., *JNCI*, vol. 78, No. 3, pp. 581–585, (Mar. 1987).
Rong, et al., *Cancer*, 57:586–590, (1986).
Penhaligon, et al., *JNCI*, vol. 74, No. 4, pp. 869–873, (Apr. 1985).
Lee, et al., *Cancer Research*, 47:5021–5024, Oct. 1, 1987.
Choay, Seminars in Thrombosis and Hemostatis, vol. 11, No. 2, pp. 81–85 (1985).
Barzu, et al., *Biochimica et Biophysica Acta*, 845:196–203 (1985).
Folkman, *New Eng. J. of Med.*, vol. 285, No. 21, pp. 1182–1186, Nov. 18, 1971.
Wadzinski, et al., *Clin. Physiol. Biochem.*, 5:200–209 (1987).
Thompson, et al., *Science*, vol. 241, 1349–1352 (1988).
Folkman, J., *Ann. Surg.*, "Anti–Angiogenesis: New Concept for Therapy of Solid Tumors," vol. 175, No. 3, pp. 409–416, Mar. 1972.
Folkman, J., *Biochemical Pharmacology*, vol. 34, No. 7, pp. 905–909 (1985).
Folkman, et al., *Science*, vol. 235, 442–447 (1987).
Folkman, et al., *Science*, vol. 243, 1490–1493 (1989).
Medhkour, et al., *J. Neurosurg.*, vol. 71, pp. 545–550 (1989).
Folkman, *Advances in Cancer Research*, vol. 43, pp. 175–203 (1985).
Lee, J.K., et al., *J. Neurosurg.*, vol. 73, 429–435 (1990).
Lee, J.K., et al., *Neurosurgery*, vol. 26, No. 4, pp. 598–605 (1990).
Lee, J.K. et al., "Inhibition of Growth and Angiogenesis of Human Neurofibrosarcoma by Heparin and Hydrocortisone", *J. Neurosurg.* 73:429–435 (Sep. 1990).
Lee, J.K. et al., "Growth of Human Schwannomas in the Subrenal Capsule of the Nude Mouse", *Neurosurgery* 26(4):598–605 (Apr. 1990).
Medhkour et al., "Implantation of Human Meningiomas into the Subrenal Capsule of the Nude Mouse", *J. Neurosurg.* 71:545–550 (Oct. 1989).
Armstrong et al., "Liquid Chromatographic Separtion of Diastereomers and Structural Isomers on Cyclodextrin–Bonded Phases", *Anal. Chem.* 57(1):234–237 (Jan. 1985).
Bergeron, R.J., "Cycloamylose–Substrate Binding",*Inclusion Compounds III*, pp. 391–443, Academic Press, London (1984).
Choay et al., "Structure–Activity Relationship in Heparin: A Synthetic Pentasaccharide with High Affinity for Antithrombin III and Eliciting High Anti–factor Xa Activity", *Biochem. Biophys. Res. Comm.* 116(2):492–499 (Oct. 31, 1983).
Frank, S.G. and Kavaliunas,, D.R., "Investigation of the β–Cyclodextrin–Hydrocortisone Inclusion Compound", *J. of Pharm. Sciences* 72(10):1215–1217 (Oct. 1983).
Saenger, W., *Inclusion Compounds*, vol. 2, pp. 235–259, Atwood et al. (Eds.), Academic Press, New York (1984).
Szejtli, J., "Industrial Applications of Cyclodextrins", *Inclusion Compounds III*, pp. 331–381, Academic Press, London (1984).
Tabushi, I., "Reactions of Inclusion Complexes Formed by Cyclodextrins and Their Derivatives", *Inclusion Compounds III*, pp. 445–471, Academic Press, London (1984).
van Boeckel et al., "Synthesis of a Potent Antithrombin Activating Pentasaccharide: A New Heparin–Like Fragment Containing Two 3–0–Sulphated Glucosamines", *Tetrahedron Letters* 29(7):803–806 (1988).

*Primary Examiner*—Kathleen K. Fonda
*Attorney, Agent, or Firm*—Sterne, Kessler, Goldstein & Fox PLLC

[57] ABSTRACT

A method for treating a neurofibrosarcoma tumor comprising administration of heparin and an angiostatic steroid is disclosed. Animal models for the growth of neurally-derived tumors and for testing therapeutic agents are also provided.

5 Claims, 4 Drawing Sheets

INHIBITION OF NEUROFIBROSARCOMA GROWTH AND ANGIOGENESIS

This application is a continuation of application Ser. No. 07/510,251, filed Apr. 19, 1990, now abandoned.

This invention was made with Government support under Contract No. NS 20025 awarded by the National Institutes of Health. The U.S. Government has certain rights in this invention.

BACKGROUND OF THE INVENTION

1. Field of the Invention

The invention relates to animal models for the growth and treatment of human neurally-derived tumors and the treatment of neurofibrosarcoma tumors using a therapeutic regimen which inhibits angiogenesis and tumor vascularization.

2. Description of the Background Art

Neurofibromatosis is an autosomal dominant genetic disorder associated with the development of multiple benign tumors and occasional malignant tumors. No effective treatment is available for either form of tumor and the malignant tumors, neurofibrosarcomas, are usually fatal despite aggressive surgical, medical, and radiotherapeutic treatment regimens (Martuza, R. L., Neurosurgery, MacGraw-Hill, Vol. 1, 1984, pp. 511–521). Therefore, new approaches for the treatment of neurofibrosarcomas would be of enormous benefit at this time.

It has become increasingly evident that angiogenesis, the formation of blood vasculature, is a fundamental and necessary event in the growth of solid tumors (Brem, S., CNS 23:440–453 (1976); Folkman, J. et al., J. Exp. Med. 133:275–288 (1971); Folkman, J., Ann. Surg. 175:409–416 (1972); Folkman, J., Adv. Cancer Res. 43:175–203 (1985); Folkman, J. et al., Science 235:442–447 (1987); Greenblatt, M. et al., J. Nat. Cancer Inst. 41:111–124 (1968); Klagsbrun, M. et al., Cancer Res. 36:110–114 (1976); Rastinejad, F. et al., Cell 56:345–355 (1989); Tannock, J. F., Br. J. Cancer 22:258–273 (1968); Tannock, J. F., Canc. Res. 30:2470–2476 (1970); Thompson, J. A. et al., Science 241 1349–1352 (1988); Zagzag, D. et al., Am. J. Pathol. 131:361–372 (1988); Ziche, M. et al., JNCI 69:483–487 (1982)). Thus, therapeutic strategies directed at disrupting this process are expected to be important. Following establishment of a blood supply, tumor cells not only begin to grow but also accquire the potential for metastasizing to distant sites by entering the circulation through this new vasculature (Folkman, J., Adv. Cancer Res., supra). Invasiveness of neoplastic cells in several in vitro, in vivo, and in situ models has indeed been linked to angiogenesis (Brem, S., Proc. Amer. Assoc. Neurol. Surgeons Ann. Meet., Washington, D.C., 1989, p. 382 (abst)).

Tumor angiogenesis is induced by soluble tumor angiogenesis factors produced by tumor cells (Folkman, J. et al., 1971, supra; Folkman, J., 1985, supra). Several angiogenic factors, such as the fibroblast growth factors ($\alpha$FGF and $\beta$FGF), angiogenin, and the transforming growth factors, TGF-$\alpha$ and TGF-$\beta$, have been purified, their amino acid sequences determined, and their genes cloned (Folkman, J. et al., 1987, supra). These studies led to a hypothesis that solid tumors are angiogenesis-dependent, and that "anti-angiogenesis" was a potential approach to tumor therapy.

The art of angiogenesis research has relied mainly on three models for the in vivo study of capillary proliferation: (1) The rabbit and rodent cornea micropocket; (2) the chicken embryo chorioallantoic membrane; and (3) the hamster cheek pouch for murine experimental tumors (Folkman, J., 1985, supra; Folkman, J. et al., 1987, supra; Greenblatt, M. et al., supra; and Zagzag, D. et al., supra).

In 1983, Folkman's group disclosed that heparin or a heparin fragment administered with cortisone, caused regression of large tumor masses and prevented metastases (Folkman, J. et al., Science 221:719–725 (1983)). Angiogenesis was inhibited when heparin, or one of its fragments lacking anti-coagulant activity, was administered simultaneously with an angiostatic steroid. This was somewhat paradoxical given the fact that heparin alone actually promotes angiogenesis in vivo and can potentiate endolthelial locomotion and proliferation in vitro. The angiostatic steroids by themselves had weak or no angiogenesis-inhibiting activity (Crum, R. et al., Science 230:1375–1378 (1985)). Potent inhibition of angiogenesis required the "pair" effect of two components.

Despite the promise of this approach, the literature reflects disparate results; some investigators have observed inhibition of tumor growth with heparin plus cortisone whereas others have not (Lee, K. et al., Canc. Res. 47:5201–5204 (1987); Penhaglion, M. et al., JNCI 74:869–873 (1985); Rorg, G. H. et al., Cancer 57:586–590 (1986); Sakamoto, N. et al. JNCI 78:581–585 (1987); and Ziche, M. et al., Int. J. Cancer 35:549–552 (1985)).

For tumors that were responsive to heparin and cortisone, oral administration of 200 units of heparin per ml of drinking water was generally found to be the minimum effective dose, and tumor regression was more rapid as the dose increased up to 1000 units/ml. However, when the heparin dose was increased further, for example, to 2000–5000 units/ml, rapid tumor growth rather than regression was observed (Crum, R. et al., 1985, supra).

The efficacy of heparin was found to depend critically on the source of the heparin. The most potent, Panheparin[R] (Abbott Laboratories), is no longer commercially available. The next most potent heparin, from Hepar, Inc., Franklin, Ohio) was noted to cause regression of reticulum cell sarcoma, but not of Lewis lung carcinoma, in mice (Folkman, J. et al., 1983, supra). Heparin preparations are frequently heterogeneous in composition, molecular size, sequence, and position of substituents (N-sulfate, O-sulfate, and glucuronic acid). This may account for the differences in anti-tumor efficacy when the heparin is used in combination with angiostatic steroids (Folkman, J. et al., Science 243:1490–1493 (1989)). However, these reports tested only malignant murine tumors which may be particularly resistant to such therapy. The ability to test anti-angiogenic agents, alone or in combination, on human tumors would be of great benefit for devising therapeutic strategies.

Animal models are important tools for studying the growth and spread of human tumors and for developing and testing therapeutic strategies. The development of congenitally athymic "nude" mice and refinement of techniques for producing immunodieficiencies in rodents have permitted more detailed study of a variety of xenotransplanted human tumors (Aamdal, S. et al., Int. J. Cancer 34:725–730 (1984); Abernathey, C. D. et al., Neurosurgery 22:877–881 (1988); Bailey, M. J. et al., Br. J. Cancer 50:721–724 (1984); Bigner, S. H. et al., J. Neuropathol. Exp. Neurol. 40:390–409 (1981); Dumont, P. et al., Int. J. Cancer 33:447–451 (1984); Epstein, A. L. et al., Cancer 37:2158–2176 (1976); Giovanella, B. et al., Adv. Cancer Res. 44:69–129 (1985); Rajnay, J. et al., Oncology 44:307–311 (1987); Rao, M. S. et al., J. Pathology 135:169–177 (1981); Schold, S. C. et al., Prog. Exp. Tumor Res. 28:18–31 (1984)).

Several human brain tumor models involving subcutaneous (s.c.) or intracerebral (i.c.) implants in nude mice, have been reported (Basler, G. A. et al., in *The Nude Mouse in Experimental and Clinical Research*, Fogh, J. et al. (eds.), New York: Academic Press, Vol. 2, pp. 475–490 (1982); Bradley, N. J. et al., *Br. J. Cancer* 38:263–272 (1978); Bullard, D. E. et al., *Neurosurgery* 4:308–314 (1979); Horten, B. C. et al., *J. Neuropathol. Exp. Neurol.* 40:493–511 (1981); O'Sullivan, J. P. et al., *J. Endocr.* 79:139–140 (1978); Rana, M. W. et al., *Proc. Soc. Exp. Biol. Med.* 155:85–88 (1977); Shapiro, W. R. et al., *J. Natl. Cancer Inst.* 62:447–453 (1979): Slagel, D. E. et al., *Cancer Res.* 42:812–816 (1982); Tueni, E. A. et al., *Eur. J. Cancer Clin. Oncol.* 28:1163–1167 (1987); Ueyama, Y. et al., *Br. J. Cancer* 37:644–647 (1978)).

In vivo models of tumors grown in nude mice have been extremely useful for a wide variety of purposes, such as studying tumor biology and testing sensitivity to chemotherapy and radiotherapy. Although s.c. xenografts allow serial tumor volume measurements, and the procedure of implantation is easy, the s.c. tumors are difficult to measure precisely with calipers since they may be surrounded by fibrous tissue or fat. Many neural tumors typically grow slowly. A short-term method for the growth of particular human tumors in mice was developed by Castro and Cass (Castro, J. E. et al., *Br. J. Surg.* 61:421–426 (1974)) and later refined by Bogden et al. (Bodgen, A. E. et al., *Cancer* 48:10–20 (1981)), using solid tumor fragments implanted under the kidney capsule.

The sub-renal capsule assay allows precise measurement (accurate to 0.1 mm) of changes in tumor size as measured using a stereomicroscope with an ocular micrometer. The sub-renal capsule contains no fat and minimal, if any, reactive fibrous tissue. Greater blood flow has been observed in sub-renal capsule tumor implants as compared to s.c. tumors, suggesting an advantage of the sub-renal capsule for delivery of both nutrients and systemically administered antitumor agents (Sands, H. et al., *Cancer Lett.* 24:65–72 (1984)). In addition, invasive and metastatic properties, not generally observed after s.c. implantation, may be observed with tumors growing under the renal capsule.

Intracerebral tumor models are thought: to mimic the clinical environment for neurally-derived tumors. However, the presence of the blood-brain barrier makes drug delivery and limitations thereto an important concern. Furthermore, studies are usually limited to only one point, survival. In contrast, sub-renal capsule tumors are accessible for direct, accurate and repeated measurements. More importantly, the extracerebral location allows investigation of the cellular sensitivity of these neoplasms to drugs with less concern about the drug delivery problem. If a tumor cell is inherently resistant to an agent, improving delivery of that agent into the brain will be of no benefit. Demonstration of cellular sensitivity of a sub-renal capsule tumor to an agent can be translated into an approach for intracerebral delivery of that agent (Schold, S. C. et al., *Prog. Exo. Tumor Res.* 28:18–31 (1984)).

Meningiomas are important and interesting examples of tumorigenesis in the human nervous system because: (1) they are relatively common and clinically important; (2) a 3:1 female:male incidence ratio suggests possible hormonal modulation; and (3) recent molecular genetic studies have demonstrated an associated abnormality on chromosome 22 (Jay, J. R. et al., *J. Neurosurg.* 62:757–762 (1985); Kaplan, J. C. et al., *J. Med. Genet.* 24:65–78 (1987); Magdelenat, H. et al., *Acta Neurochir.* 64:199–213 (1982); Markwalder, M. T. et al., *Surg. Neurol.* 30:97–101 (1988); Martuza, R. L. et al., *Neurosurgery* 9:665–671 (1981); Mirimanoff, R. O. et al., *J. Neurosurg.* 62:18–24 (1985); Olson, J. J. et al., *J. Neurosurg.* 66:584–587 (1987); Olson, J. J. et al., *J. Neurosurg.* 65:99–107 (1986)).

Another neurally-derived tumor, the Schwannoma, appears most frequently in humans as an acoustic neuroma which is a benign tumor formed by Schwann cells of the eighth cranial nerve (Rubinstein, L. J., Armed Forces Institute of Pathology, Washington, D.C., pp. 205–214 (1972)). Most acoustic neuromas occur unilaterally in a sporadic, non-hereditary fashion, whereas bilateral acoustic neuromas are associated with neurofibromatosis-2 (NF2), a serious autosomal dominant genetic disorder associated with multiple Schwannomas, neurofibromas, acoustic neuromas, ependymomas, and astrocytomas (Martuza, R. L. et al., *N. Engl. J. Med.* 318:684–688 (1988)). Recent molecular genetic studies have revealed that both unilateral nonhereditary acoustic neuromas as well as those associated with NF2 are related to a deletional mutation or an inactivating mutation of a putative growth suppressor gene on chromosome 22 (Seizinger, B. R. et al., *Nature* 322:644–647 (1986); Seizinger, B. R. et al., *Science* 236:317–319 (1987)). This gene has not yet been cloned, and its function is unknown. However, it would be important to have a model system for study and genetic manipulation of the growth of human acoustic neuromas. To date, no such model exists.

Clinically, acoustic neuromas are the most common tumors in the cerebello-pontine angle, and despite modern surgical and anesthetic techniques, they remain a serious surgical challenge. Although most can be totally removed, some are very vascular or recurrent. This is particularly problematic in the NF2 patient who faces the possibility of bilateral deafness, facial paresis, or other neurologic dysfunction. No medical treatment is currently of proven efficacy to modify the growth of these tumors (Martuza, R. L. et al., *Neurosurgery* 10:1–12 (1982); Martuza, R. L. et al., *N. Engl. J. Med.* 318:684–688 (1988)).

The study of Schwannomas is also important from the standpoint of Schwann cell biology and molecular mechanisms of growth control. Two endogenous mitogens have been demonstrated to stimulate Schwann cell mitosis. One is a membrane-associated mitogen found in the neurite axon and the other, termed glial growth factor (GGF), is a soluble mitogen normally found in the pituitary and in the caudate nucleus. Human acoustic neuromas have very high levels of a mitogen similar to, or identical with, GGF, and suggest the possibility that the growth of Schwannomas is self-stimulated by an autocrine mechanism (Martuza, R. L. et al., *TINS* 11:22–27 (1988); Martuza, R. L. et al., *N. Engl. J. Med.* 318:684–688 (1988)). Other studies have demonstrated elevated levels of FGF mRNA in acoustic neuromas (Murphy, P. R. et al., *Mol. Endocrinol.* 3:225–231 (1989)).

Finally, the study of Schwannomas is important for our understanding of the genetic mechanisms of tumorigenesis. Studies both of NF2 bilateral acoustic neuromas as well as of non-hereditary unilateral acoustic tumors suggest that both types of acoustic neuromas are related to a loss or inactivation of a tumor suppressor gene on the long arm of chromosome 22 (Seizinger, B. R. et al., 1986, 1987, supra).

To date, there are no useful techniques for studying the growth behavior of Schwannomas in a controlled laboratory setting. Study of human brain tumors in vitro has limitations. For example, studies based on monolayer cell culture or organ culture do not reflect in vivo morphology, neovascularization, or growth characteristics of the original tumor (Horten, B. C. et al., *J. Neuropathol. Exp. Neurol.* 40:493–511 (1981)). Appenzeller et al. (Appenzeller, O. et al., *J. Neurol. Sci.* 74:69–77 (1986)) transplanted Schwann cells of the aural nerve, neurofibrosarcomas, and a malignant Schwannoma from three neurofibromatosis patients into sciatic nerves of immunosuppressed mice. However, that study was designed to evaluate myelination, not tumor formation.

In summary, there is an acute need in the art for animal models of human neurally-derived tumors for basic understanding of tumor growth regulation, tumor metastasis, as well as for development of treatment modalities. Furthermore, novel forms of therapy of human neurally-derived tumors such as neurofibrosarcomas are urgently needed.

BRIEF SUMMARY OF THE INVENTION

The present invention is based on the inventors' recognition that malignant tumors of peripheral nerve are associated with neovascularity, and that therapeutic strategies targeted to tumor angiogenesis should be efficacious in treating such tumors which are associated with neurofibromatosis in humans.

In one embodiment, the invention is directed to a nude mouse model system to evaluate the effects of therapeutics on human neurally-derived tumors. This model comprises growth of tumor cells derived from the fresh tumor or from cultured tumor cells under the renal capsule of the nude mouse. The invention is directed to the use of this animal model to evaluate therapeutic agents. In a preferred embodiment, the therapeutic agent is a combination of an angiostatic steroid and heparin or a fragment or synthetic substitute thereof. By inhibiting angiogenesis and neovascularization, this agent inhibits tumor growth.

The invention is directed in particular to a method for treating a neurofibrosarcoma comprising the administration of an effective amount of heparin, a heparin fragment, or a synthetic heparin substitute and an angiostatic steroid or steroid derivative to an animal in need of such treatment.

DESCRIPTION OF THE PREFERRED EMBODIMENTS

Figure 1:
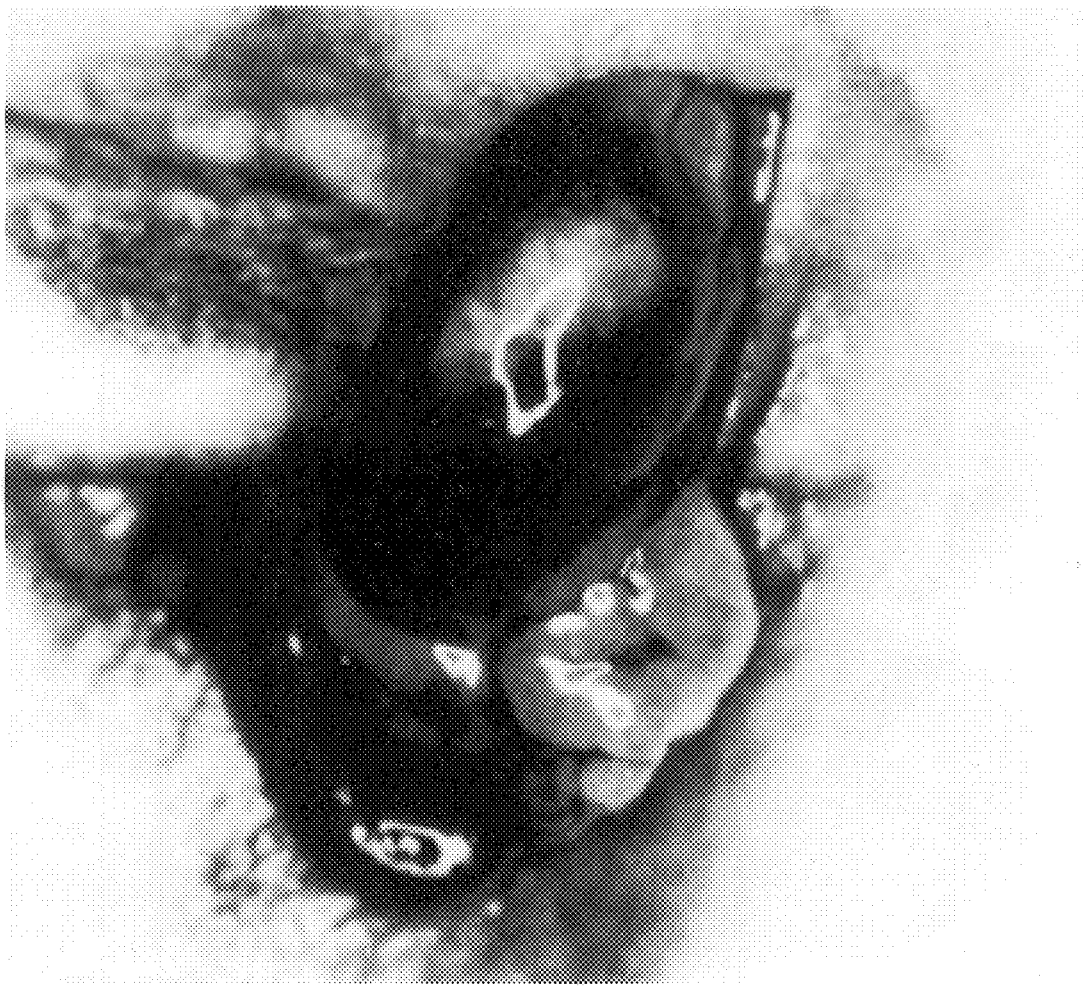
FIG. 1. Solid tumor implant of meningioma in subrenal capsule of nude mouse 4 weeks after implantation. The kidney is exposed for tumor volume measurement. Note the vascularity of the tumor (arrowheads).

An animal model has been developed by the inventor for studying the growth of human neurally-derived tumors, and for evaluating the therapeutic efficacy of anti-tumor agents.

By the term "neurally-derived" as used herein is intended tumors which originate in the nervous system and tumors which develop from cells which originate from the embryonic neural crest. Such tumors include, but are not limited to meningiomas, Schwannomas (for example, acoustic neuromas), neurofibrosarcomas, ependymomas, gliomas, and pheochromocytomas.

The animal model of this invention has several advantages including: (1) the histologic appearance of the original tumor is retained in the subcapsular site in vivo; (2) tumor size and vascularity can be measured serially using an ocular microscope; (3) there is no adipose or fibrous tissue to confound accurate tumor measurement; and (4) tumor take is high. This model system permitted the development and evaluation of therapeutic regimens for human neurofibrosarcoma, based on the use of angiostatic steroids and heparin, which comprise an additional embodiment of this invention.

This invention is directed to a method for treating a neurofibrosarcoma tumor in an animal comprising administering an effective amount of a combination of heparin and an angiostatic steroid.

By the term "treating" is intended amelioration or cure of the tumor, which includes the cessation of growth, the regression or disappearance of a detectable solid tumor, or a prevention or diminution in metastasis of the tumor.

The term "substantially associated with" neurofibromatosis means that the tumor is one of the pathological manifestations of neurofibromatosis and occurs in a significant percentage of neurofibromatosis patients.

The preferred animal subject of the present invention is a mammal. By the term "mammal" is meant an individual belonging to the class Mammalia. The invention is particularly useful in the treatment of human subjects, although it is intended for veterinary uses as well.

In addition to heparin, included in the scope of the present invention is the use of a heparin fragment or a synthetic heparin substitute in the treatment of neurofibrosarcoma.

The variable activity of different heparin preparations in the inhibition of angiogenesis in combination with steroid is known in the art. Heparin preparations are nonuniform and heterogeneous in composition, molecular size, structure, position of substituents (N-sulfate, O-sulfate, and glucuronic acid), and sequence (Goldgaber, et al., *Science* 235:877 (1987); Tanzi et al., Science 235:881 (1987); Robakis, N. K et al., *Proc. Natl. Acad. Sci. USA* 84:4190 (1987)). This heterogeneity is thought to be responsible for various effects observed.

Heparin can be modified, or heparin fragments synthesized by methods known in the art (Choay, J et al., *Biochem. Biophys. Res. Comm.* 116:492 (1983); van Boeckel, C. A. A. et al., *Tetrahedron Lett.* 29:803 (1988), both of which references are hereby incorporated by reference).

Preferred heparin fragments include a hexasaccharide or a pentasaccharide fragment. Preferred synthetic heparin substitutes comprise cyclodextrins of six to eight glucopyranose units. A more preferred cyclodextrin is β-cyclodextrin tetradeasulfate.

Cyclodextrins are naturally occurring cyclic nonreducing, water-soluble oligosaccharides built up from six to eight glucopyranose units (Bender, M. L. et al., *Cyclodextrin Chemistry*, Springer Verlag, Berlin, 1978); Saenger, W., *Angew. Chem. Int. Ed. Engl.* 91:344 (1980); Saenger, W., In: *Inclusion Compounds* (Atwood, J. L. et al., eds.), Academic Press, New York, 1984, vol. 2, pp. 232–259). (The preceding 3 references and the other references to cyclodextrins, cited below, are hereby incorporated by reference.)

The internal doughnut-shaped molecule provides a hydrophobic cavity at the center and a hydrophilic outer surface. The diameter of the cavity is determined by the number of glucose units that make up the ring (6,7, or 8 units for α-, β-, γ-cyclodextrins, (respectively). Steroids or other hydrophobic molecules with appropriate structures can form complexes with cyclodextrins (Bergeron, R. J., In: *Inclusion Compounds* (Atwood, J. L. et al., eds.), Academic Press, New York, 1984, vol. 3, pp. 391–443; Tabushi, I., ibid, pp. 391–443;and Szejti, J., ibid, pp. 331–338). An inclusion complex between hydrocortisone and β-cyclodextrin has been demonstrated (Frank, S. G. et al., *J. Pharm. Sci.* 72:1215 (1983); Anderson, F. M. et al.,*Arch. Pharm. Chemi. Sci. Ed.* 11:61 (1983); Armstrong, D. W. et al.,*Anal. Chem.* 57:234 (1985)). Cyclodextrins have 18 to 24 hydroxyl units exchangeable for substituents that could increase the hydrophilic and cell-binding activity of the carrier molecule. Various of the α-, β-, γ-cyclodextrins have angiostatic activity in combination with hydrocortisone and cortexolone (see: Folkman, J. et al., 1989, supra).

The present invention is intended to include all cyclodextrins with angiostatic activity, such as tetrapropoxy-β-cyclodextrin, tetradecamethoxy-β-cyclodextrin, β-cyclodextrin heptasulfate, β-cyclodextrin tetradecasulfate, α-cyclodextrin dodecasulfate, and γ-cyclodextrin hexadecasulfate. A preferred cyclodextrin is β-cyclodextrin tetradecasulfate.

The term "angiostatic steroid" describes a newly defined class of steroids, based on a particular biological activity, inhibition of angiogenesis. The classification of steroids as glucocorticoids, mineralocorticoids, or as biologically inactive steroids, is inapplicable for identifying angiostatic steroids. Thus, steroid molecules of both known biological classes, and even molecules devoid of known bioactivity, can function as angiostatics (see Crum, R. et al. (1985), supra, which is hereby incorporated by reference). Furthermore, angiostatic activity may be highly concentration-dependent. For example, dexamethasone at 50–60 µg (the optimal angiostatic concentration of hydrocortisone) is not angiostatic in the presence of heparin. A sharp peak of angiostatic activity is detected at 2 µg of dexamethasone (24-fold the activity of hydrocortisone). However, 3 to 200 µg of dexamethasone shows no angiostatic activity.

The preferred angiostatic steroids (natural and synthetic) of this invention include, but are not limited to, hydrocortisone, 11α-epihydrocortisol, cortexolone, 17α-hydroxyprogesterone, corticosterone, desoxycorticosterone, testosterone, estrone, dexamethasone, triamcinolone, and 6α-fluoro-17,21-dihydroxy-16β-methyl-pregna-4,9,(11)-diene-3,20-dione.

In addition to steroids, the invention includes steroid derivatives, such as those formed metabolically in the liver during steroid inactivation by enzymatic reduction of the 4,5 double bond in the A ring to form the dihydrosteroid derivative. This is further converted into a tetrahydro derivative by the enzymatic reduction of the 3-oxo group to a 3-hydroxyl group. These derivatives are rendered water-soluble during metabolic inactivation by conjugation to glucuronic acid and are subsequently excreted by the kidney. Although considered biologically inactive (Liddle, G. W. et al., *Textbook of Endocrinology*, R. H. Williams, Ed., Saunders, Philadelphia, 5th Ed., 1974, p. 244), the dihydro and tetrahydro derivatives retain angiostatic activity in the presence of heparin (Crum et al., supra).

The preferred angiostatic steroid derivatives of this invention include dihydro and tetrahydro steroid derivatives.

As used herein, an "effective amount of a combination" is meant to refer to an amount of a combination of heparin, a heparin fragment, or a synthetic heparin substitute with an angioclenic steroid, that is sufficient to cause cessation of growth, regression or disappearance of a tumor, or a diminution in its metastasis, in a subject recipient.

The specific amount of heparin and steroid required by each individual will be dependent upon the age, health, and weight of the recipient, kind of concurrent treatment, if any, frequency of treatment, and the nature of the effect desired. Generally, daily dosages of heparin will be from about 10 to about 50,000 units per kg of body weight. Preferably, from 50 to 2000 units/kg/d, in one or more applications per day, is effective to obtain the desired result. Most preferably, a daily dose from about 70 to about 350 units/kg/day is given. In an alternative approach, the heparin, particularly where formulated in a timed-release form, may be administered less frequently, i.e., every other day or every third day. Depending on the steroid used, the daily dose of steroid will be from about 1 to about 100 mg/kg body weight. Preferably, from about 5 to about 25 mg/kg is effective to obtain the desired results.

Depending on the particular steroid or spheroid derivative used, and the particular heparin, heparin fragment, or synthetic heparin substitute used, the effective dose can be varied, as will be apparent to one of skill in the art.

The combination heparin and steroid treatment of the present invention may be administered by any means, routes, or pharmaceutical compositions that achieve their intended purpose. Amounts and regimens for the administration of heparin and any particular steroid can be determined readily by those with ordinary skill in the art. For example, administration may be by parenteral, subcutaneous, intravenous, intramuscular, intrapulmonary, intraperitoneal, intranasal, transdermal, or buccal routes. Alternatively, or concurrently, administration may be by the oral route.

For treatment according to the invention, heparin and the steroid are administered simultaneously, or within a proximity of hours between separate administration of each component of the combination. Thus, for example, a dose of the heparin may be given up to 12 hours before or after a dose of steroid. The preferred timing of administration is simultaneous.

The pharmaceutical composition may be employed in dosage form such as tablets, capsules, powder packets, or liquid solutions, suspensions, or elixirs, for oral administration, or sterile liquid for formulations such as solutions or suspensions for parenteral use.

Preparations for parenteral administration include sterile aqueous or non-aqueous solutions, suspensions, and emulsions. Carriers or occlusive dressings can be used to increase skin permeability and enhance cutaneous absorption.

The invention also relates to a medicament or pharmaceutical composition comprising heparin and an angiogenic steroid, the medicament being used for treating a neurofibrosarcoma which may be substantially associated with neurofibromatosis.

The invention is also directed to a nude mouse implanted in its renal capsule with a human neurally-derived tumor, and the use of such a mouse as a model to study growth and evaluate treatment of the implanted tumors. Use of nude mice for xenotransplantation of human tumors is well known in the art (Fogh, J. et al. (eds.), *The Nude Mouse in Experimental and Clinical Research*, New York: Academic Press, Vol. 2, pp. 475–490 (1982), which is hereby incorporated by reference.

Congenitally athymic nude mice of either sex, such as CD-1 nu/nu mice from Charles River Laboratories (Wilmington, Mass.) weighing between about 20 and 30 grams are used. Mice are preferably housed in sterile cages in groups of five, and given autoclaved chow and water ad libitum.

Surgery is preferably performed under sterile conditions. Each mouse is anesthetized by administration of a general anesthetic. For example mice are given an intraperitoneal injection of 0.3 ml of a 4% chloral hydrate solution, and this is supplemented with ether inhalation when necessary (Bogden, A. E. et al., *Cancer* 48:10–20 (1981)]; (Fingert, H. J. et al., *Proc. Natl. Acad. Sci. USA* 81:7927–7931 (1984), which references are hereby incorporated by reference). An oblique incision of about 1-cm length is maje in a region of the left flanks which is preferably made aseptic by application of an antiseptic sterilizing solution such as 70% ethanol. Using a stereomicroscope, the kidney capsule is lifted with microforceps, and a tumor implant of about 0.5 to 2 mm in size, either from the surgical specimen or from cell cultures in a fibrin clot, is placed under the renal capsule by means of a needle or trochar of an appropriate gauge to hold the fragment (such as a 19 gauge needle). The implant is mobilized 1 to 2 mm away from the capsule opening to prevent adhesions. Nylon suture, for example of 5.0 gauge, is used for closure in a single layer.

Preparation of a cell pellet or cell cluster from culture for implantation is performed by methods well-known in the art. The cell pellet is suspended in a mixture of, for example, fibrinogen and thrombin and incubated at about 37° C. for about 5 to 10 minutes to obtain a solid fibrin clot matrix (Fingert, H. J. et al., supra).

Tumor growth from the implanted fragment, cell pellet or cluster is evaluated by measurement of two perpendicular diameters of the implant using, for example, an ocular micrometer in the eyepiece of a stereomicroscope. Tumor volume is estimated from the formula (volume=length×width×½) (Fingert, H. J. et al., supra).

The same surgical and anesthetic techniques are used to make serial tumor volume measurements, the first being performed upon implantation and the following measurement at about 10 to 21 days after tumor implantation into the subrenal capsule. These times may vary depending upon the type of tumor and its rate of growth as will be appreciated by one of skill in the art. The animals can be reexamined four or five additional times during a three-month period to generate growth curves for each individual tumor.

Tumor vascularity can be graded as follows: grade 0=no visible vessels; grade I=one or two vessels; grade II=three or four vessels; grade III=more than four vessels. Typically, at the end of a study, the animals are humanely sacrificed for histological examination.

Having now generally described the invention, the same will be more readily understood through reference to the following example which is provided by way of illustration, and is not intended to be limiting of the present invention, unless specified.

EXAMPLE I

A Model for Studies of Tumor Growth and Treatment: Growth of Human Meningiomas in the Sub-Renal Capsule of the Nude Mouse A reproducible model is needed for the study of a variety of human neurally derived tumors from both surgical specimens and tissue culture. Below is a study of the growth and histological characteristics of human meningiomas implanted into the subrenal capsule of the nude mouse.

I. Materials and Methods

A. Preparation from Surgical Specimen

Human meningiomas were obtained at surgery. After the initial diagnosis by frozen section evaluation, further specimens were submitted for routine pathological studies. The remainder as divided into three portions: one was frozen at −80° C. for hormonal or DNA studies; a second was used for tissue culture is described below; and another portion was cut into 1-mm pieces in a Petri dish containing nutrient medium, F10 supplemented with 10% fetal calf serum (FCS) and antibiotics (penicillin, fungizone, and streptlomycin) (all obtained from GIBCO, Life Technologies, Inc., Grand Island, N.Y.). The 1-mm pieces were implanted into the subrenal capsule of the nude mouse within 1 to 2 hours of the surgical procedure.

B. Preparation from Monolayer Cell Cultures

One-millimeter pieces of tumor were digested with collagenase II and incubated for 1 hour. Nutrient medium was added, and the mixture centrifuged at 500×g for 10 minutes. The cell pellets were suspended in nutrient medium and plated in 75-mm tissue culture flasks (Model Nunc:Kamstrupvej 90, DK-4000, manufactured by Kamstrup, Roskilde, Denmark). These cells were maintained at 37° C. in a gas mixture of 95% $O_2$ and 5% $CO_2$ for three to four passages. For animal implantation, monolayer cultures were resuspended with trypsin-ethylenediaminetetra-acetic acid (EDTA) solution (0.5 gm of trypsin and 0.2 gm of EDTA/liter) and washed with nutrient medium containing FCS, and the cells were counted. Five to $10 \times 10^6$ were centrifuged into a 1.5-ml microcentrifuge tube at 500×g for 5 minutes. The cell pellet was suspended in 12 $\mu$l of fibrinogen and 6 $\mu$l of thrombin (Sigma Chemical Co., St. Louis, Mo.) and incubated at 37° C. for 5 to 10 minutes to obtain a solid fibrin clot matrix (Fingert, H. J. et al., *Proc. Natl. Acad. Sci. USA* 81:7927–7931 (1984)). This solidified pellet was cut into 1-mm pieces for surgical implantation.

C. Surgical Procedure

Congenitally athymic female nude mice (nu/nu CD-1) (Charles River Laboratories, Wilmington, Mass.) weighing 22–28 gm were housed in sterile cages in groups of five, and given autoclaved chow and water ad libitum. The surgery was performed in a designated nude mouse facility under sterile conditions. Each mouse was anesthetized with an intraperitoneal injection of 0.3 ml of a 4% chloral hydrate solution supplemented with ether inhalation when necessary (Bogden, A. E. et al., *Cancer* 48:10–20 (1981)]; Fingert, H. J. et al., supra). An oblique 1-cm incision was made in a sterilized (70% ethanol) region of the left flank. Under a stereomicroscope (with ocular micrometer accurate to 0.1 mm), the kidney capsule was lifted with a microforceps, and the tumor implant (0.5 to 2 mm), either from the surgical specimen or from cell cultures in a fibrin clot, was placed under the renal capsule by means of a modified No. 19 needle. The implant was then mobilized 1 to 2 mm away from the capsule opening to prevent adhesions. Measurement of two perpendicular diameters of the tumor implant was made using the ocular micrometer. Tumor volume was estimated from the formula (volume=length×width×½) (Fingert, H. J. et al., supra). Nylon 5.0 suture was used for closure in a single layer.

The same surgical and anesthetic techniques were used to make serial tumor volume measurements, the first being performed 10 to 21 days after tumor implantation into the subrenal capsule (FIG. 1). The animals could be reexamined four or five additional times during a three-month period to generate growth curves for each individual tumor. Tumor vascularity was graded as follows: grade 0=no visible vessels; grade I=one or two vessels; grade II=three or four vessels; grade III=more than four vessels. At the end of the study, the animals were humanely sacrificed for histological examination.

D. Histological Analysis

Samples of tumors successfully grown in the nude mice were fixed in 10% buffered formalin and embedded in paraffin. Hematoxylin and eosin-stained sections were compared with the original, routinely processed pathological specimens.

II. Results

Meningiomas from 16 different patients (three males and 13 females) were implanted in the subrenal capsule of the nude mice. In 8 experiments, the animals were implanted only with solid tumors from the surgical specimens. In 4 experiments the tumor implants were prepared only from monolayer cultures of meningioma cells embedded in a fibrin clot. In 4 experiments tumors were implanted via both techniques. In each experiment 10 to 24 nude mice were used.

A. Growth Characteristics

Figure 2A:
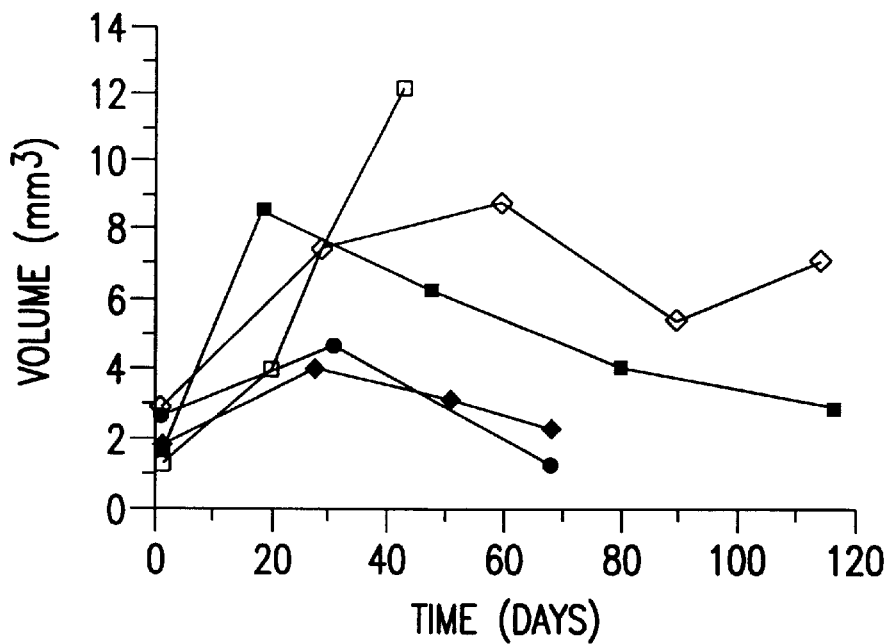
FIG. 2. Ten of 12 solid tumor implants displayed growth and neovascularity in the subrenal capsule. Growth curves are shown for 10 tumors, five in 2A and five in 2B. The initial mean volumes, maximal mean volumes, and corresponding standard deviations and histology are shown in Table 1.
Figure 2B:
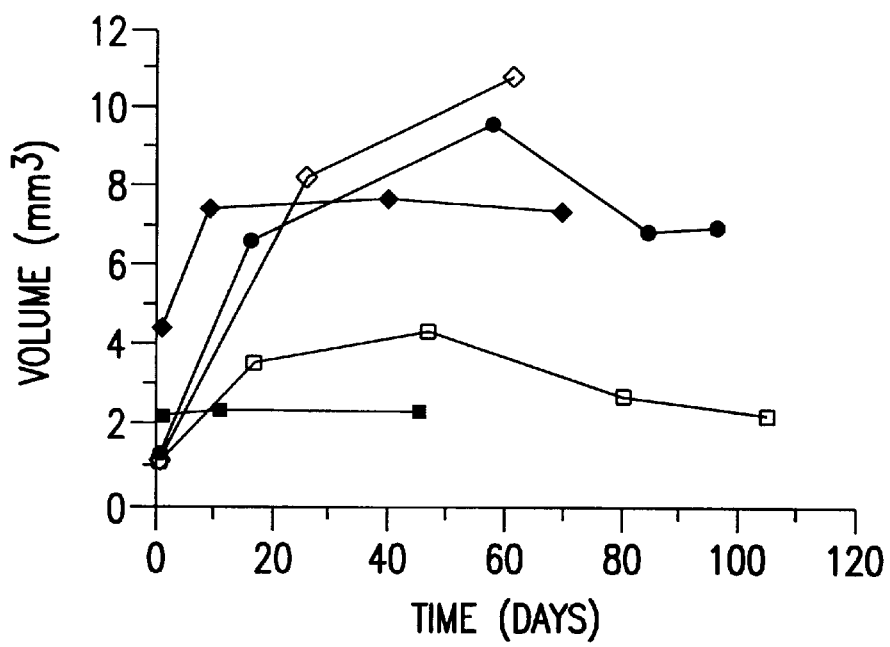

1. Solid Tumor Implants. At the first surgical reopening performed within 10 to 21 days after implantation, 10 of the 12 tumors in the solid implant group showed an increase in volume in most of the animals (>90%) of each group. Most of the tumors showed a two- to threefold increase in volume (FIG. 2). Neovascularity was present and increased as the tumors grew larger. Tumor growth reached its peak at 6 to 7 weeks postimplantation (Table 1); the volume then either stabilized or decreased. Hence, 83% of tumors derived directly from the surgical specimen were successfully grown in this model system.

TABLE 1

VOLUME OF SOLID MENINGIOMA IMPLANTS ON DAY 1 AND ON DAY OF MAXIMAL MEASURED GROWTH*

| Tumor Number | First Mean Volume | Maximal Mean Volume (Day) | Vascularity Grade** | Implant Histology |
|---|---|---|---|---|
| 1 | 1.3 ± 0.7 | 12.1 ± 1.9 (43) | II | Typical |
| 2 | 1.7 ± 0 | 4.0 ± 0 (28) | I | Typical |
| 3 | 2.6 ± 1.0 | 4.6 ± 1.3 (31) | I | Atypical |
| 4 | 2.9 ± 1.1 | 8.8 ± 4.7 (60) | II | Typical |
| 5 | 1.8 ± 1.4 | 8.6 ± 5.0 (19) | III | Typical |
| 6 | 1.1 ± 0.5 | 4.4 ± 1.6 (46) | II | Typical |
| 7 | 4.4 ± 3.3 | 7.6 ± 4.3 (39) | III | Atypical |
| 8 | 1.3 ± 0.9 | 9.5 ± 5.0 (57) | II | Typical |
| 9 | 1.1 ± 1.6 | 10.7 ± 4.4 (60) | III | Malignant |
| 10 | 2.2 ± 2.6 | 2.3 ± 1.9 (11) | II | Atypical |

*Mean volumes of tumor implants and standard deviations (mm$^3$) were measured on Day 1 and the day of maximal measured tumor growth (given in parentheses). Implant histology was similar to that of the original specimen in all cases: benign typical fibroblastic; transitional meningotheliomatous; or atypical highly cellular with rare mitotic figures. The malignant meningioma displayed mitotic figures, necrosis, and kidney invasion by the implant.
**Grade 0 = no visible vessels; Grade I = one or two vessels; Grade II = three or four vessels; Grade III = more than four vessels.

Figure 3A:
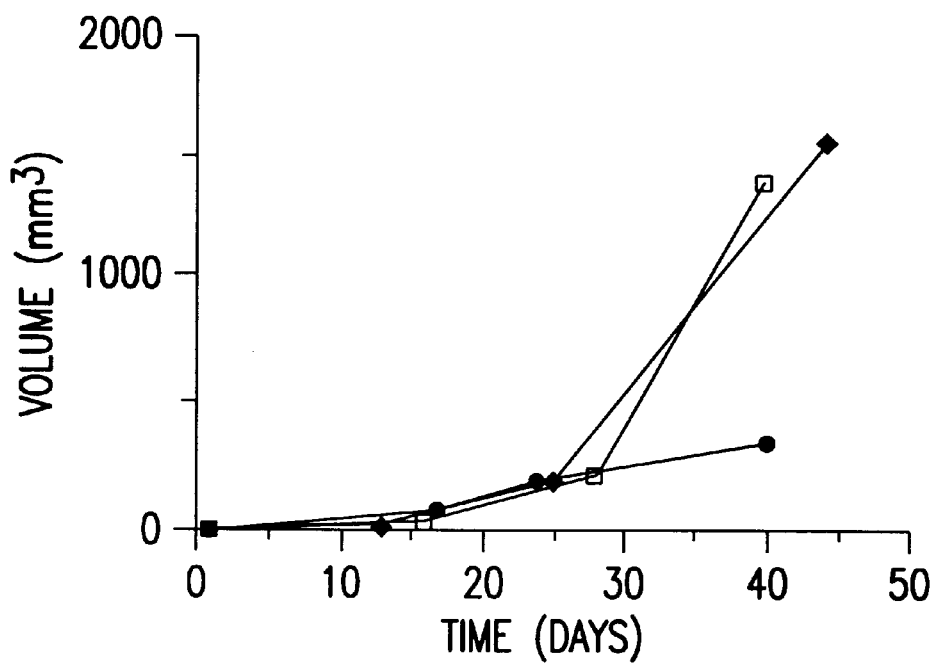
FIG. 3. Six tumor implants grew from cell cultures. The three that grew most rapidly are shown in 3A, and slower growing implants are shown in 3B. Note the difference of the scale of volume on the vertical axes. The initial mean volumes, maximal mean volumes, and corresponding standard deviations and histology are shown in Table 2.
Figure 3B:
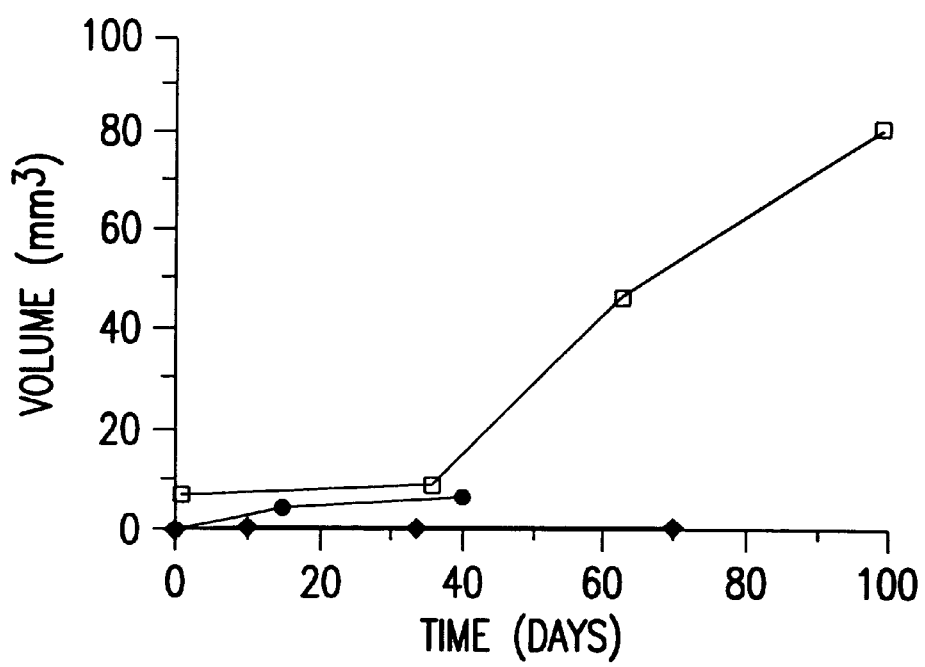

2. Cell Culture Implants. Eight of the tumors were implanted using tissue culture cells embedded in a fibrin clot. Six (75%) of these tumors grew successfully. Three tumors grew at a rate similar to that noted in the solid implant group whereas three tumors grew more rapidly and reached 10 to 20 times the initial volume in the first two weeks (FIG. 3). In these three latter experiments, extensive tumor growth necessitated early sacrifice of the mice at 7 weeks postimplantation (Table 2). There was a difference in growth characteristics in only one of the four tumors that were grown both as a solid tumor implant and from cell culture. Two tumors displayed satisfactory growth by both techniques. One tumor did not grow via either technique, and one grew only from the solid implant.

To evaluate growth characteristics of possible fibroblast contamination in these early-passage cell lines, nonmalignant human fibroblasts (WI38) were implanted in two experiments by the same fibrin clot technique. Similar to results reported by Fingert et al. (supra), these nonmalignant cells did not grow.

TABLE 2

VOLUME OF MENINGIOMA IMPLANTS DERIVED FROM CELL CULTURES ON DAY 1 AND ON DAY OF MAXIMAL MEASURED GROWTH*

| Tumor Number | First Mean Volume | Maximal Mean Volume (Day) | Vascularity Grade** | Implant Histology |
|---|---|---|---|---|
| 1 | 0.6 ± 0.4 | 1383 ± 514 (40) | III | Malignant |
| 2 | 0.4 ± 0.3 | 1543 ± 1453 (44) | II | Malignant |
| 3 | 1.3 ± 1.8 | 335 ± 99 (40) | II | Malignant |
| 4 | 7.0 ± 4.7 | 81.2 ± 8.4 (98) | I | Atypical |
| 5 | 0.7 ± 0.1 | 0.8 ± 0.7 (34) | I | Typical |
| 6 | 0.8 ± 0.2 | 6.4 ± 1.6 (40) | II | Malignant |

*Mean volume of tumor implants and standard deviations (cu mm) were measured on Day 1 and the day of maximal measured tumor growth (given in parentheses). The first three tumors from cell cultures, although benign in the original tumor specimen, displayed characteristic features of malignant meningioma in the implant specimen. The last three tumors retained their original histological features.
**Grade 0 = no visible vessels; Grade I = one or two vessels; Grade II = three or four vessels; Grade III = more than four vessels.

B. Histological Findings

The original pathology specimens consisted of 13 benign typical meningomas, two atypical meningiomas, and one malignant meningioma. The solid tumor implants of typical benign meningiomas (either fibroblastic, transitional, or meningotheliomatous) grown in the subrenal capsule were virtually identical to the histological patterns seen in the original surgical specimens. The atypical and malignant meningiomas also retained their histological features and there was focal infiltration of the mouse kidney by the one malignant meningioma we studied.

In contrast, three of the four benign tumors implanted from cell culture showed malignant histological features including high cellularity, mitotic figures, foci of necrosis, and fewer whorls. These tumors appeared to be mesenchymal neoplasms with focal spindle-cell fibrosarcomatous, and pseudopapillary patterns, characteristic of malignant meningiomas (Russell, D. S. et al., *Pathology of Tumors of the Nervous System*, Ed. 4, Baltimore: Williams & Wilkins, pp. 63–100 (1977)). The one malignant meningioma implanted from cell culture retained its aggressive characteristics. None of the tumors were lymphomas (Brooks, S. E. et al., *Lab. Invest.* 58:518–523 (1988)). A mixed acute and chronic inflammatory infiltrate was observed in one of these tumors and was attributed to the presumed presence of infection. One atypical meningioma and one typical meningioma transplanted in this manner retained the appearance of the original tumor.

III. Discussion

Although most solitary meningiomas can be surgically cured, some cannot be completely resected and may recur (Mirimanoff, R. O. et al., *J. Neurosurg.* 62:18–24 (1985)).

It would be important to have a model system that allows the study of potentially useful therapeutic methods for treating neural tumors such as the meningiomas described above. Current meningioma models have specific limitations: studies in monolayer cell culture do not reflect in vivo morphology, neovascularity, or growth characteristics (Olson, J. J. et al., *J. Neurosurg.* 65:99–107 (1986)); subcutaneous xenografts allow serial tumor volume measurements, but growth is slow and the measurements may be inaccurate due to fibrous and fatty tissue adjacent to the tumor (Kubo, O. et al., *Neurol. Surg.* 11:369–377 (1983); Olson, J. J. et al., *J. Neurosurg.* 66:584–587 (1987); Rana, M. W. et al., *Proc. Soc. Exp. Biol. Med.* 155:85–88 (1977); Ueyama, Y. et al., *Br. J. Cancer* 37:644–647 (1978)); intracerebral xenografts and other methods of brain-tumor transplants do not easily allow for multiple measurements of tumor volume (Basler, G. A. et al., in Fogh, J. et al. (eds.), *The Nude Mouse in Experimental and Clinical Research*, New York: Academic Press, Vol. 2, pp. 475–489 (1982); Constans, J. P. et al., *Neurochirurgie* 6:501–510 (1965); Horten, B. C. et al., *J. Neuropath. Exp. Neurol.* 40:493–511 (1981)). Additionally, long-term studies or growth of sizeable tumors is precluded by neurological deterioration or death of the animal.

Because of the cost of nude mice, initially the subrenal capsule assay was used in CD-1 mice immunosuppressed with cyclosporine (Fingert, H. J. et al., supra). However, since meningiomas are benign and grow slowly, either they were immunologically rejected or the mice died of cyclosporine complications before satisfactory tumor growth could be achieved.

We therefore have used the subrenal capsule of the nude mouse as a model for growth of human neural tumors such as meningiomas. This model is attractive for multiple reasons: (1) the surgical procedure is simple; (2) tumor volume does not threaten the life of the host, as may be the case when tumor cells are intracerebrally implanted; (3) serial tumor volumes can be measured using an ocular micrometer which is more precise than caliper measurements of subcutaneous tumors; (4) tumor take is high; (5) there is no need for additional immunosuppression; and (6) although nude mice are prone to infection it seldom occurred, and did not hinder measurements of tumor growth (Basler, G. A. et al., supra; Fingert, H. J. et al., supra). Furthermore, acute inflammation was absent in the majority of the implants.

The results of these experiments achieved 83% tumor take using solid tumor implants and 75% using cultured cells embedded in a fibrin clot. The average duration of an assay was 8 to 10 weeks. Growth curves of meningiomas demonstrated a persistent volume increase during the first 8 weeks. This tumor enlargement correlated well with neovascularity, which expanded as the tumor reached a peak at 6 to 8 weeks. The histology of the directly implanted tumors was similar to that of the original human tumor. As in other reports, we found that a fibrin clot matrix of the tumor cells facilitated the growth of transplanted tumors (Fingert, H. J. et al., *Cancer Res.* 47:3824–3829 (1987)). This may relate to alterations in tumor cell interactions with the extracellular matrix, resulting in more rapid proliferation and aggressive growth of the fibrin clot-embedded meningioma cells (Pauli, B. U. et al., *Hum. Pathol.* 19:628–639 (1988)).

Meningiomas are more common in women and may enlarge during pregnancy (Bickerstaff, E. R. et al., *J. Neurol. Neurosurg. Psychiatry* 21:89–91 (1958); Mirimanoff, R. O. et al., *J. Neurosurg.* 62:18–24 (1985)). Women with breast cancer are more prone to develop meningiomas (Schoenberg, B. S. et al., *Neurology* 25:705–712 (1975)). Multiple studies have shown estrogen and progesterone binding in meningiomas, and hormonal modulation as a therapeutic tool merits further investigation (Gottardis, M. M. et al., *J. Steroid Biochem.* 30:311–314 (1988); Gravanis, A. et al., *J. Clin. Endocrinol. Metab.* 60:156–163 (1985); Herrmann, W. et al., *C. R. Seances Acad. Sci.* 294:933–938 (1982); Magdelenat, H. et al., *Acta Neurochir.* 64:199–213 (1982); Markwalder, M. T. et al., *Surg. Neurol.* 30:97–101 (1988); Olson, J. J. et al., *J. Neurosurg.* 65:99–107 (198(6); Yamada, K. et al., *Gan To Kagaku Rvoho* 13:1241–1248 (1986)).

The subrenal capsule assay of the nude mouse is a feasible model for future studies of hormonal modulation of tumors susceptible to such modulation, as is the case with meningiomas. Also, since meningioma cells can be manipulated in cell culture and then implanted by these same techniques, this model may allow investigations at the cellular and molecular levels, including the interactions of tumor suppressor genes and oncogenes on tumor progression (Seizinger, B. R. et al., *Proc. Natl. Acad. Sci. USA* 84:5419–5423 (1987)).

EXAMPLE II

A Model for Studies of Tumor Growth and Treatment: Growth of Human Schwannomas in the Sub-Renal Capsule of the Nude Mouse Herein, we report our investigations of the growth of human Schwannomas as xenografts in the nude mouse sub-renal capsule as a novel method for studying the growth of these cells.

I. Materials and Methods

A. Tumor Implant Preparation from Surgical Specimens

Human Schwannomas were obtained from surgery. After the initial diagnosis of Schwannomas by frozen section evaluation, further specimens were submitted for routine pathologic studies. The remainder was divided into several portions; one was frozen at −80° C. for DNA studies; a second was cut into 1 mm$^3$ pieces in a Petri dish containing nutrient medium, supplemented F10, described above. The minced tumor pieces were implanted into the sub-renal capsule of the nude mouse within 1 to 2 hours of the surgical procedure. The remaining portion of the surgical specimen was used for cell cluster by enzymatic dispersion as described below.

B. Tumor Implant Following Enzymatic Dispersion

One mm$^3$ tumor pieces were digested with collagenase (Worthington Biotechnical Corporation, Halls Mills Road, Freehold, N.J. 07728) and trypsin (GIBCO) in 3.2 ml DMH (Dulbecco's Modified Eagle's Medium: GIBCO+20 mM HEPES: (SIGMA) and incubated for 30 minutes. Nutrient medium was added. Centrifugation at 500×g was done for 10 minutes, after which the cell pellets were resuspended in Hanks' balanced salt solution (GIBCO) and centrifuged at 500×g for 5 minutes. The cell pellet was mixed with 15 μl of fibrinogen (SIGMA) and 8 μl of thrombin (SIGMA), and incubated at 37° C. for 5 to 10 minutes to obtain solid fibrin clot matrix (Fingert, H. J. et al., 1987, supra). This solidified pellet was cut into 1 mm$^3$ pieces for the surgical implantation.

C. Surgical Procedure

Congenitally athymic female nude mice (nu/nu CD-1, see above) were housed as above, and surgery was performed essentially as described in Example I, above. Measurement of tumor size was performed as in Example I.

Using the same surgical and anesthetic techniques, serial tumor volume measurements were made, the first being performed 20–30 days after implantation into sub-renal capsule. The animals were reexamined 2 or 3 additional times during a 1.5 to 3 month period to generate growth curves for each individual tumor. Tumor vascularity was graded as follows: grade 0=no visible vessels; grade 1=vessels occupied one quarter of tumor surface; grade 2=vessels occupied a half of tumor surface; grade 3=vessels occupied three quarters of tumor surface; grade 4=vessels occupied more than three quarters of tumor surface. At the end of the study, the animals were humanely sacrificed for histological examination, D. Histologic Analysis Histological analysis was performed as in Example I. The Schwann cell composition of the implanted Schwannomas in the sub-renal capsule was confirmed by immunohistochemical staining for S-100 protein. For immunoperoxidase staining on formalin-fixed paraffin-embedded sections the S-100 protein antiserum produced in rabbit (Dako Corp., Santa Barbara, Calif.) was used at a dilution of 1:800 using an avidin-biotinylated immunoperoxidase (ABC) method (Sobel, R. A. et al., *J. Immunol.* 132:2393–2401 (1984)). Deparaffinized sections were incubated sequentially in normal goat serum, rabbit anti-S100, dilute $H_2O_2$ biotinylated goat anti-rabbit Ig, and horseradish peroxidase coupled with avidin-biotin complex, with washes in phosphate buffered saline between each step. The reaction product was visualized with 3-amino-9-ethylcarbazole (AEC) and the slides were counterstained with hematoxylin. Controls included substitution of normal rabbit serum for anti-S100 serum.

E. DNA Analysis

Genomic DNA was prepared from the following tissues: a fresh acoustic neuroma obtained immediately after surgery, the same acoustic neuroma three weeks after its implantation in the subrenal capsules of five different nude mice, and mouse renal tissue adjacent to the implanted tumors (Seizinger, B. R. et al., supra). Lambda phage DNA was used as a control. Tissue was frozen in liquid nitrogen and then minced into a fine powder using a mortar and pestle. The powder was then digested at 55° C. overnight in a buffer that contained 10 mM Tris-HCl, pH=7.3, 1 mM sodium chloride, 100 mM EDTA and 10 mg/ml of proteinase K. After multiple extractions with phenol/chloroform/isoamyl alcohol (25:24:1), DNA was precipitated in 2 volumes of ice-cold ethanol and 0.2 M KCl. Genomic DNA was then either recovered by low-speed centrifugation or was directly spooled out of this solution using a glass pipette. After redissolving in 10 mM Tris-HCl pH=7.3, 1 mM EDTA, DNA concentrations were determined by measuring optical densities at 260 nM.

After digestion with the restriction enzymes EcoRI or BamHI, the DNA was analyzed on a 1% agarose gel. DNA was then transferred onto a Hybond membrane (Amersham) using the method of Southern (Southern, E., *J. Mol. Biol.* 98:503 (1975)). The filter was prehybridized overnight at 65° C. in 6×SSC/1×Denhardt's/0.3% SDS and 0.1 mg/ml of denatured salmon sperm DNA. Hybridization was then carried out in the same buffer for 3 days at 65° C. The hybridization probe consisted of a linearized 800 base pair fragment of the human Alu 1 repetitive sequence (Jelinek, W. R. et al., *Ann. Rev. Biochem.* 51:813–844 (1982)). This probe had been radioactively labeled with a P32 dATP using the primer-directed method (Feinberg, A. P. et al., *Anal. Biochem.* 137:266–267 (1984)). The hybridized filter was then washed extensively and successively in 3×SSC, 2×SSC, 0.5×SSC and 0.1×SSC at 65° C. for 30 minutes each. Autoradiography was carried out at −70° C. for 3 hours.

II. Results

Tumor specimens from 14 different patients (13 acoustic neuromas, 1 trigeminal Schwannoma) were implanted into the sub-renal capsule of nude mice (Table 3). In 11 experiments, the animals were implanted only with solid tumor from the surgical specimens. In 2 experiments, the tumor implants were made from solid tumors and cell clusters. In 1 experiment, the tumor implants were made only from cell clusters. Each experiment utilized 3 to 12 nude mice. Eighty-four nude mice survived at least two measurements and 24 nude mice survived only one measurement.

A. Growth Characteristics

Figure 4A:
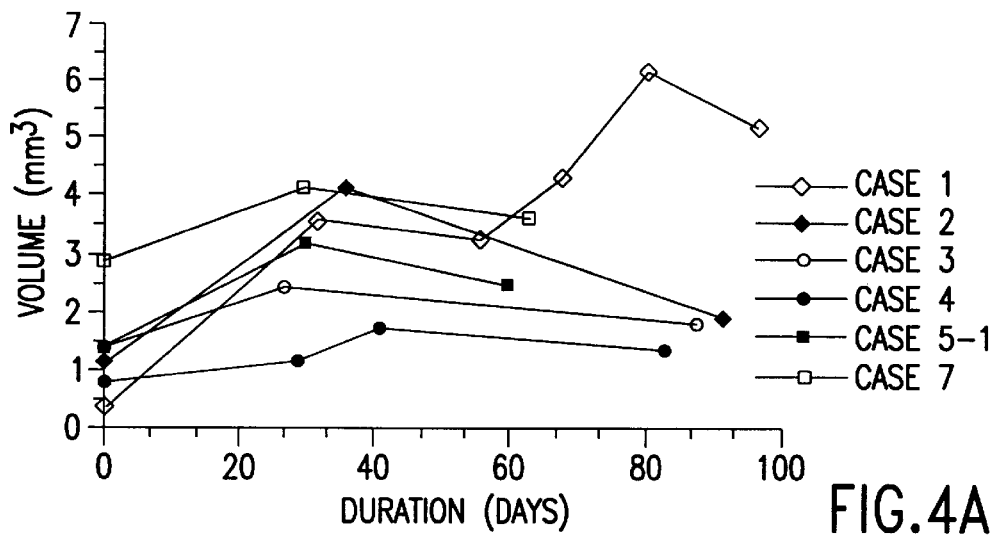
FIG. 4. The mean growth of Schwannomas in the subrenal capsule of nude mice of each case. Tumors grew during 3 to 5 weeks. A,B) fresh solid tumor fragments, C) tumor cell clusters.
Figure 4B:
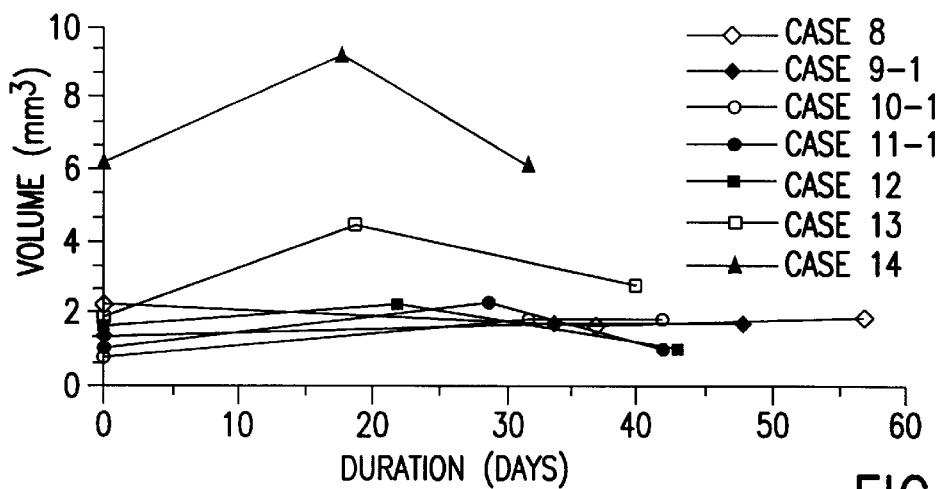
Figure 4C:
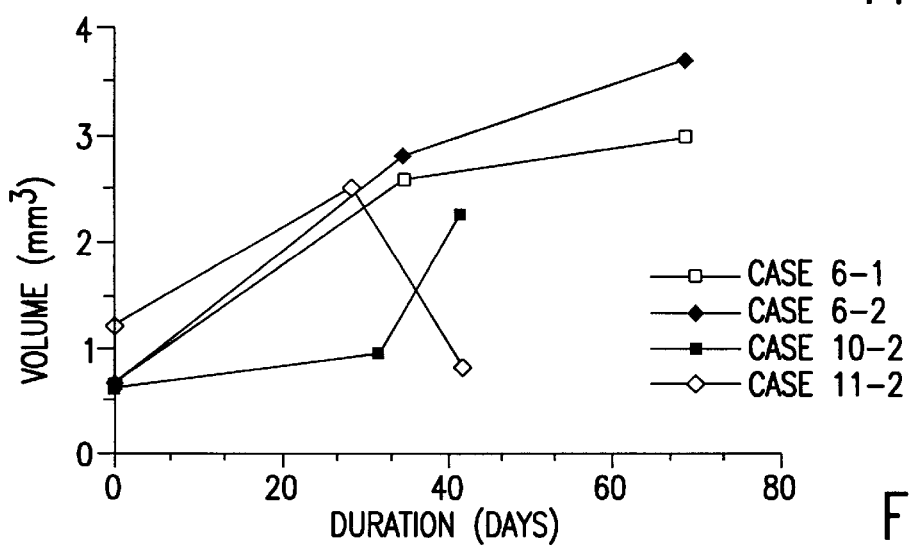

Tumor specimens from 14 different patients were implanted into the sub-renal capsule of 108 nude mice, including 88 animals with solid tumor specimens and 20 animals with cell clusters by enzymatic dispersion (Table 3). Tumors which grew or showed no regression were considered useful tumors for further experiments. The percentage of useful tumors in each type of implant were 77.3%; in solid tumors, 70% in cell clusters. Mean tumor growth of each specimen is shown in FIGS. 4A–4C. Maximum tumor volume varied as did time span to reach that volume. Fifty-nine of 84 animals which were measured at least twice showed tumor growth and this growth showed three different patterns: (1) In 37 animals, implanted tumors initially grew and then maintained same size, regressed or disappeared. 2) In 21 animals, implanted tumors grew continuously during the experiment. (3) In only one animal, the implanted tumor regressed and then grew. Tumor implants in 67 animals (62.0%) grew in 3 to 5 weeks after implantation. Enlarging tumors and stable tumors showed marked neovascularity. Regressing tumors and those that disappeared showed minimal or no neovascularity (Table 4).

To evaluate growth characteristics of possible fibroblast contamination, human fibroblasts (W138) ($1.5 \times 10^6$ cells per animal) were implanted in 2 experiments (5 animals per experiment) by the same techniques. These non-neoplastic cells regressed. When the animals were examined at one to two weeks after fibroblast implantation, no fibroblasts or vascularization were seen.

TABLE 3

RESULTS OF SCHWANNOMA IMPLANTS

| | Implant | | | No. of Animals in Which Tumor Size:* | | | |
|---|---|---|---|---|---|---|---|
| Case | (S or C) | Days | Total | + | 0 | − | x |
| 1 | S | 97 | 10 | 8 | 1 | | 1 |
| 2 | S | 92 | 9 | 7 | 1 | 1 | |
| 3 | S | 88 | 10 | 9 | 1 | | |
| 4 | S | 83 | 10 | 5 | 4 | | 1 |
| 5 | S | 60 | 5 | 5 | | | |
| 6-1 | C | 69 | 6 | 4 | 1 | | 1 |
| 6-2 | C | 69 | 5 | 3 | 1 | 1 | |
| 7 | S | 63 | 6 | 3 | 1 | 1 | 1 |
| 8 | S | 57 | 4 | | 2 | | 2 |
| 9 | S | 48 | 4 | 2 | | 2 | |
| 10-1 | S | 42 | 4 | 3 | | | 1 |
| 10-2 | C | 42 | 5 | 1 | 1 | 2 | 1 |
| 11-1 | S | 42 | 4 | 1 | | 1 | 2 |
| 11-2 | C | 42 | 4 | 2 | 1 | | 1 |
| 12 | S | 43 | 5 | 1 | | 1 | |

TABLE 3-continued

RESULTS OF SCHWANNOMA IMPLANTS

| Case | Implant (S or C) | Days | Total | No. of Animals in Which Tumor Size:* | | | |
|------|------------------|------|-------|---|---|---|---|
|      |                  |      |       | + | 0 | − | x |
| 13   | S                | 40   | 5     | 4 |   | 1 |   |
| 14   | S                | 32   | 12    | 10|   | 1 | 1 |
| TOTALS |              |      | 108   | 68| 14| 11| 15|
| % OF TOTAL IMPLANTS | |      | (100) |(63)|(13)|(10)|(14)|

*Changes in tumor size: + = increased; 0 = unchanged; − = decreased; x = disappeared.
Tumor specimens from 13 different patients (13 acoustic neuromas; 1 trigeminal Schwannoma; case #8) were implanted into the sub-renal capsule of 108 nude mice. The specimen of case 11 was from an acoustic neuroma of a NF2 patient. The two implant techniques used fresh solid tumor fragments (S = solid) and tumor cell clusters by enzymatic dispersion (C = cluster). The cluster was suspended in a fibrin matrix. In case 6-1, one cluster was suspended in nude mouse blood clot.

TABLE 4

THE RELATION OF TUMOR SIZE AND NEOVASCULARITY

| Neovascularity Grade | No. of Animals in Which Tumor Size:* | | | |
|---|---|---|---|---|
|   | + | 0 | − | x |
| 4 | 21 | 3 | 1 |   |
| 3 | 34 | 3 | 2 |   |
| 2 | 9  | 2 | 3 |   |
| 1 | 4  | 2 | 1 | 3 |
| 0 |    |   | 2 | 12|
| Totals | 68 | 10 | 15 | 15 |

*Changes in tumor size: + = increased; 0 = unchanged; − = decreased; x = disappeared.
Tumor neovascularity was graded: 0 = no visible vessels; 1 = vessels occupied ¼ of tumor surface; 2 = vessels occupied ½ of tumor surface; 3 = vessels occupied ¾ of tumor surface; 4 = vessels occupied more than ¾ of tumor surface.

B. Histology

The tumors which grew or remained a stable size but did not regress appeared as well encapsulated oval mass in the sub-renal capsule space compressing and indenting the kidney surface without any parechymal invasion. The implanted tumors showed spindle cells which are very similar to the original tumor, but have less cellularity and more hyalinized background than the original tumor. The implanted cells contained S-100 protein immunoperoxidase stain. The implanted tumors have Antoni A type pattern without Antoni B areas. No definite Varocay bodies and palisading were seen, although some of the original tumor had definite Verocay bodies and palisading.

There are no significant microscopic differences among groups receiving solid tumor implants or cell clusters. The original pathology specimen from case 3 showed some nuclear pleomorphism with moderate cellularity but without mitosis. All ten solid tumor implants from this specimen achieved successful growth. However, only two showed pleomorphic nuclei similar to the original specimen. The remaining eight showed regular nuclei without pleomorphic nuclei. Some of the implanted tumors had a mononuclear inflammatory cell infiltration (mainly lymphocytic) at the periphery of the grown tumor. Three implants showed foreign body giant cells at the periphery of tumor. Fifteen implants disappeared by the first reopening. These mice showed a thickened renal capsule at the site of operation.

C. DNA Analysis

To genotypically evaluate the origin of the implanted acoustic neuromas, Southern blot analysis was carried out on a tumor that had been freshly removed from a patient at surgery, and on the same tumor specimen after it had been implanted in the sub-renal capsule of five mice. Approximately 2.5 μg of DNA for tumors and 5 μg for the kidneys was restricted with EcoRI or BamFI and analyzed using a primer-directed radioactively labeled probe (Feinberg, A. P., et al., *Anal. Biochem.* 137:266–267 (1984)). The hybridized probe was the human AluI repetitive sequence which is found exclusively in human tissues, and thus will not hybridize to murine DNA. (Jelinek, W. R. et al., *Ann. Rev. Biochem.* 51:813–844 (1982)). After digestion with either EcoRI or BamHI, both the freshly obtained acoustic neuroma DNA and the implanted tumors strongly hybridized to the human AluI probe, whereas DNA from mouse kidney did not.

III. Discussion

Because of the cost of nude mice, we initially used the sub-renal capsule assay in CD-1 mice immunosuppressed with cyclosporine. However, since acoustic neuromas are benign and grow slowly, they were either rejected or the mice died of cyclosporine complications before satisfactory tumor growth could be achieved. Therefore we tested the sub-renal capsule of the nude mouse as a model site for growth of human acoustic neuromas and other Schwannomas. We find no evidence that this tumor has previously been xenotransplanted into the sub-renal capsule of the nude mouse. We have used several implant techniques for improving the growth of tumor in the sub-renal capsule of the nude mice. Fresh solid tumor fragments arid tumor cell clusters could achieve 77.3% and 70% tumor growth or maintenance, respectively. Tumor enlargement and stability correlated well with neovascularity of the Schwannomas, and regressing tumors showed minimal or no neovascularity.

The human origin of the implanted tumors is confirmed by the AluI hybridization of the tumors' DNA. It appears that the amount of DNA loaded for the original acoustic neuroma is less than the amount of DNA loaded for the implanted acoustic neuroma or mouse kidney when increasing amounts of DNA are loaded on a gel and compared. Thus, we cannot exclude the possibility that some of the DNA in the implanted acoustic neuroma, which can be visualized by loading increasing amounts of EcoRI cut DNA and visualizing via ethicium bormide staining of agarose gels, represents DNA from mouse cells. However, the very strong hybridization with the AluI probe by the implanted acoustic neuroma and the absence of hybridization by the mouse kidney DNA indicates the human origin of the implanted tumor. The Schwann cell origin of the implanted tumor is confirmed by the presence of S-100 protein in both the original tumor and in the implant. This excludes the possibility that the implanted tumors represent the growth of fibroblasts.

The study of Schwannomas is important both for clinical reasons and for improving our understanding of Schwann cell biology and molecular mechanisms of growth control. The development of a model such as this will provide for the study of therapeutic regimens to alter tumor growth or vascularity. The nude mouse sub-renal capsule assay also provides the ability to study the effects of genetic alterations of Schwannoma cells. Thus, this technique can be used in elucidating the function of the gene causing acoustic neuromas and neurofibromatosis-2.

EXAMPLE III

The animal model described above for growing human meningiomas and Schwann cell tumors (Examples I and II, respectively) allows direct observation of tumor size and neovascularity, thus permitting quantitative evaluation of the anti-tumor and anti-angiogenesis effects of a therapeutic strategy. In this study, treatment of a human neurofibrosarcoma transplanted into nude mice was with heparin, hydrocortisone, and a combination of heparin and hydrocortisone was tested.

I. Materials and Methods

A. Tumor Implant Preparation from Surgical Specimens

A human neurofibrosarcoma was obtained at surgery from a patient with multiple plexiform neurofibromas but no "cafe-au-lait" spots, Lisch nodules, acoustic neuromas, or family history of neurofibromatosis. After the initial diagnosis by frozen section histologic evaluation, further specimens were submitted for routine pathologic studies. The remainder was divided into one portion which was frozen at $-80°$ C. for DNA studies and another portion which was cut into 1 mm$^3$ pieces in a Petri dish containing FC10 medium supplemented with 10% fetal bovine serum, penicillin, streptomycin, and fungizone (GIBCO, Grand Island, N.Y.) for implantation or study.

B. Tumor Implantation in Nude Mice

The minced tumor pieces were implanted into the subrenal capsule of nude mice within 1 to 2 hours of the surgical procedure, essentially as described in Example I. Each mouse was anesthetized with intraperitoneal (i.p.) injection of 0.3 ml of avertine (2,2,2-tribromoethanol and tert-amyl alcohol (Aldrich Chemical Co., Milwaukee, Wis.). A solid tumor which grew beneath the kidney capsule of one nude mouse was removed, minced into small pieces (as above) and transferred to 78 additional mice for this study.

C. Assessment of Tumor Growth and Vascularization

Tumor growth was assessed as described above. On the 14th day after implantation, the animals were reoperated and tumor size and degree of neovascularization were determined.

The animals were randomly assigned to 4 different treatment groups: 1) control (with or without antibiotics), 27 animals; 2) oral heparin (200 units/ml or 500 units/ml), 17 animals; 3) oral hydrocortisone (0.3 mg/ml), 10 animals; 4) oral heparin (200, 500 or 1000 units/mi) with hydrocortisone (0.3 mg/ml), 24 animals. After 10 days of treatment, the animals were humanely sacrificed and tumor size and degree of neovascularization were again determined.

Tumor vascularity was graded as follows: grade 0=no visible vessels; grade 1=vessels occupied one quarter of tumor surface; grade 2=vessels occupied a half of tumor surface; grade 3=vessels occupied three quarters of tumor surface; grade 4=vessels occupied more than three quarter of tumor surface. The grading was done independently by two observers and was documented in coded photographs.

D. Preparation of Heparin, Steroid, and Antibiotic Solutions

Sodium heparin (157 U/mg) from porcine intestinal mucosa (Hepar Industries, Franklin, OH) was administered in sterile drinking water at concentration of 200, 500, or 1000 units/ml. Hydrocortisone-21-phosphate disodium salt (Sigma, St. Louis, Mo.) was administered at a concentration of 0.3 mg/ml in sterile drinking water. To minimize the mortality due to infections in hydrocortisone treated animals, 250 mg/L of terramycin (oxytetracycline HCl, Pfizer Agricultural Div., New York, N.Y.) and 250 mg/L of Polymyxin B (Upjohn, Kalamazoo, Mich.) were added to the drinking water, and the drinking water was filtered using Nalge$^R$ disposable filterware (0.2 mm pore size; Nalgene, Rochester, N.Y.). These antibiotics were given to the animals for a 10-day period starting on day 14 after tumor implantation.

E. Histologic Analysis

Portions of the kidneys with implanted tumor samples were analyzed histologically as described above. The degree of tumor invasion into the kidney was scored for each sample in which a sufficient amount of transplanted tumor could be identified (n=39). Each slide contained five sections of kidney. The maximum numbers of invasive foci were determined in each sample and generally ranged from 0 to 3. A score of 4 was assigned for four or more foci of invasion (n=6 samples). Evaluation of invasion was performed by an observer who had no knowledge of the treatment each animal had received.

F. DNA Analysis

Genomic DNA was prepared from the following tissues: the fresh neurofibrosarcoma obtained immediately after surgery, the same neurofibrosarcoma 24 days after its implantation in the subrenal capsule of five different nude mice, and mouse renal tissue adjacent to the implanted tumors (Seizinger, B. R. et al., Nature 322:644–647 (1986)). Tissue preparation, DNA preparation, and DNA analysis were performed as described above.

G. Statistical Analysis

The tumor volume and tumor growth rate for each group was analyzed using one-factor ANOVA. Angiogenesis was evaluated using the Chi square statistic. The results of tumor invasiveness were evaluated using one-factor ANOVA. A p value less than 0.005 was chosen as the level of significance (Matthews, D. E. et al., eds., *Using and Understanding Medical Statistics*, Karger (1985)).

II. Results

A. Growth Characteristics

In preliminary experiments, most animals that received 0.3 or 0.45 mg/ml of hydrocortisone in their drinking water did not survive longer than 2 weeks. However, all animals treated with 0.3 mg/ml of hydrocortisone plus antibiotics survived at least 10 days. To exclude possible direct effects or cross reactions of antibiotics with heparin, we also added antibiotics to the other treatment groups. No difference in tumor growth was observed in antibiotic-treated (n=6) compared to completely untreated control animals (n=21) (p>0.1).

As shown in Table 5, the control group and the heparin-only group showed an increase in the size of the implanted neurofibrosarcoma, but the heparin-treated group showed more tumor growth than the control group (p<0.001). There were no differences in the effect on tumor growth between 200 units/ml and 500 units/ml of heparin (p>0.5) and we have therefore combined groups. By contrast, all of the heparin plus hydrocortisone treatment groups had either no significant increase or showed regression in the tumor size (p<0.001 vs. controls). Although there were no statistically significant difference in 3 different heparin dosages when combined with hydrocortisone (p>0.5), one animal in the highest dosage heparin group (1000 units/ml and hydrocortisone 0.3 mg/ml) demonstrated a complete regression of the implanted neurofibrosarcoma. However, many animals given this high dose of heparin with or without hydrocortisone died or appeared sick, so that we could not extend further study with this dosage. Tumor size in the hydrocortisone group was statistically less than that in the control group (p<0.05), suggesting a minimal role for hydrocortisone alone in inhibition of tumor growth. However, tumor growth in the heparin plus hydrocortisone groups were not only different from the controls (p<0.001) but were also significantly different from the hydrocortisone only group (p<0.05). Thus, treatment with heparin and hydrocortisone was more effective than hydrocortisone alone in inhibiting the growth of malignant neurofibrosarcoma (Table 5).

TABLE 5

Growth of Implanted Tumors

| | N | Mean Tumor Volume (mm3) on Day: 0 | 14 | 24 | Net Change on Days: 0–14 | 14–24 |
|---|---|---|---|---|---|---|
| Control | 27 | 4.31 (0.51) | 4.06 (0.56) | 12.24 (1.35) | −0.24 | 8.18 |
| Heparin (200 & 500 u/ml) | 17 | 4.96 (0.63) | 3.71 (0.81) | 16.86 (2.81) | −1.24 | 13.15 |
| Hydrocortisone (0.3 mg/ml) | 10 | 4.02 (0.43) | 2.89 (0.42) | 6.53 (1.53) | −1.13 | 3.63 |
| Heparin + Hydrocortisone | | | | | | |
| 200 + 0.3 | 11 | 4.15 (0.77) | 6.65 (0.96) | 5.44 (1.49) | 1.51 | −0.21 |
| 500 + 0.3 | 9 | 4.33 (0.44) | 5.56 (1.30) | 5.59 (1.27) | 1.23 | 0.33 |
| 1000 30 0.3 | 4 | 2.59 (0.68) | 2.81 (1.12) | 1.37 (0.62) | 0.22 | −1.45 |

Values in parenthesis are standard errors.

There were no significant differences (p>0.5) in tumor size among the groups on day 0 and 14. Tumor growth over days 0–14 (prior to initiation of treatment) was not different between the groups (p>0.5). During the treatment period (from day 14 to day 24), the control, heparin only, and hydrocortisone only groups all showed increases in tumor size. The tumor were larger in the heparin group compared to the control group (p<0.001), whereas hydrocortisone significantly suppressed tumor growth (p<0.05). In contrast, in all of the heparin plus hydrocortisone treatment groups, tumors either regressed or showed no significant growth (p<0.001 vs controls).

B. Angiogenesis Characteristics

Since there was no statistical difference in tumor growth between the antibiotic-treated and antibiotic untreated controls, we combined these groups in order to have enough animals for statistical evaluation of the neovascularity. We also combined the two heparin groups (200 units/ml and 500 units/ml) as noted above. A correlation was observed between tumor growth and angiogenesis. The control group increased the percentage of total vascularization of the implanted tumor bed (grade 3+4) from 40.7% to 85.2% during the 10 treatment days (Table 6). Heparin increased the percentage of grade 3+4 vascularity from 40% to 70%. However, heparin plus hydrocortisone reduced the percentage of the grade 3+4 vascularity from 62.5% to 29.1% during the treatment period. This result significantly differs from the control group (p<0.001).

TABLE 6

Vascularity of Implanted Tumors

| | | | Percent of Tumors with Grade: | | | | |
|---|---|---|---|---|---|---|---|
| Treatment | Day | N | 0 | 1 | 2 | 3 | 4 |
| Control | 14 | 27 | 0 | 22.2 | 37.0 | 33.3 | 7.4 |
| | 24 | 27 | 0 | 0 | 14.8 | 33.3 | 51.9 |
| Heparin | 14 | 17 | 23.5 | 17.6 | 35.3 | 17.6 | 5.9 |
| | 24 | 17 | 0 | 0 | 17.6 | 17.6 | 64.7 |
| Hydrocortisone | 14 | 1 | 10.0 | 30.0 | 20.0 | 20.0 | 20.0 |
| Heparin | 14 | 24 | 0 | 4.2 | 33.3 | 45.8 | 16.7 |
| + Hydrocortisone | 24 | 24 | 12.5 | 37.5 | 20.8 | 20.8 | 8.3 |

Angiogenesis increased as the tumor grew in heparin (combined 200 units/ml and 500 units/ml), control, and hydrocortisone (0.3 mg/ml) treatment groups. However, heparin plus hydrocortisone treatment reduced the percentage of the grade 3+4 vascularity during the treatment period (p<0.001 versus control group).

C. Histology

The tumor implants had a smooth external surface and were confined by the renal capsule. They were composed of closely packed, spindle cells which formed intertwining bundles typical of sarcoma. The nuclei were hyperchromatic and there were numerous mitotic figures and focal karyorrhexis. This histologic pattern predominated in the original surgical pathology specimen. No areas of neural differentiation or necrosis were seen in the implants. Inflammation was minimal.

Cell clusters extended from the main tumor into the parenchyma between renal tubules, resulting in isolation of tubules from neighboring tubules by invading tongues of tumor. Heparin treatment did not significantly influence the extent of invasion. However, hydrocortisone treatment alone and hydrocortisone plus heparin resulted in fewer foci of invasion compared too mice treated with heparin alone (p<0.005). There were no significant differences between the two hydrocortisone treatment groups (Table 7).

TABLE 7

Invasiveness of Implanted Tumors

| | Number | Mean invasiveness score ± SEM |
|---|---|---|
| Control | 6 | 1.5 ± 0.7 |
| Heparin | 10 | 2.6 ± 0.5 |
| Hydrocortisone | 8 | 0.38 ± 0.26 |
| Heparin + Hydrocortisone | 15 | 1.0 ± 0.3 |

The degree of tumor invasion into the kidney was scored for each sample in which sufficient amount of transplanted tumor could be identified (total number=39). Heparin (200 units/ml and 500 units/ml) alone did not significant influence the extent of invasion. However, hydrocortisone (0.3 mg/ml) alone and hydrocortisone plus heparin resulted in a lower invasiveness score (fewer foci of invasion) compared to mice treated with heparin along (p<0.005).

D. DNA Analysis

To demonstrate the human origin of tumors that had been implanted in the subrenal capsules, DNA from the original neurofibrosarcoma, from the neurofibrosarcoma that had been implanted for 24 days in the murine kidney, and from murine kidneys was digested with EcoRI, and increasing amounts of each of the DNA samples were analyzed by Southern blotting (Southern, E., *J. Mol. Biol.* 98:503 (1975)). To provide a quantitative estimate of human sequences present in the isolated DNAs, increasing amounts of each of these DNAs were separated by electrophoresis. To detect the presence of human sequences, hybridization was carried out with an artificially cloned Alu probe (Blur-8). The Alu repetitive sequence occurs exclusively in humans (Jelinek, W. R. et al., *Ann. Rev. Biochem.* 51:813–844 (1982)). Therefore, hybridizations will not occur between Alu and murine DNA. When a Southern blot analysis was performed on increasing amounts of EcoRI cut DNA the Alu probe hybridized to the original neurofibrosarcoma DNA and to the implanted tumor DNA but not to the murine kidney DNA. When we compared equal amounts of ECORI cut DNA via southern blotting, using the artificially cloned Alu probe (Blur-8), we obtained approximately the identical autoradiographic signal. We thus conclude that the implanted tumor consists almost exclusively of human and not murine cells.

III. Discussion

Hybridization with the human specific Alu probe demonstrated the human origin of the implanted tumors. This excludes the possibility that the human tumor cells somehow induced formation of a murine tumor. In fact, the vast majority of DNA from the implanted tumor is human.

The results confirmed the synergistic action of heparin and hydrocortisone in inhibiting tumor growth and angiogenesis. This is the first demonstration of such action on a human neurofibrosarcoma. The mechanism of angiogenesis inhibition by heparin-cortisone is unknown (Folkman, J. et al., *Science* 221:719–725 (1983); Ingber, D. et al., *Lab. Inves.* 59:44–51 (1988)). It is possible that one of the compounds facilitates the rapid uptake of the other into endothelial cells. An alternative interpretation is that heparin contains both a promoter and an inhibitor of angiogenesis and that only the latter acts in the presence of cortisone. Cortisone has immunosuppressive side effects leading to increased vulnerability to infection. Therefore, steroids with anti-angiogenic activity but lacking immunosuppressive activity are preferred. Heparin (after its anticoagulant activity has been eliminated) may contain both positive and negative angiogenesis regulatory activity (Folkman, J., *Biochem. Pharmacol.* 34:905–909 (1985)). The heparin fragments and synthetic substitutes which do not have these adverse effects are preferred for therapy (Folkman, J. et al. (1989), supra).

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A method for inhibiting both angiogenesis and the growth of a human neurofibrosarcoma substantially associated with neurofibromatosis in a mammal comprising administering to said mammal and effective amount of a combination of A. heparin or B. a heparin fragment selected from the group consisting of hexasaccharide pentasaccharide fragments or C. a synthetic heparin substitute selected from the group consisting tetrapropoxy-β-cyclodextrin, tetradecamethoxy-β-cyclodextrin, β-cyclodextrin heptasulfate, β-cyclodextrin tetradecasulfate, α-cyclodextrin dodecasulfate, and γ-cyclodextrin hexadecasulfate together with D. an angiostatic steroid selected from the group consisting of hydrocortisone, 11α-epihydrocortisol, cortexolone, 17α-hydroxyprogesterone, corticosterone, desoxycorticosterone, testosterone, estrone, dexamethasone, triamcinolone, and 6α-fluoro-17,21-dihydroxy-16β-methyl-pregna-4,9(11)-diene-3,20-dione or E. a dihydro or tetrahydro angiostatic steroid derivative.

2. The method of claim 1 wherein said synthetic heparin substitute is β-cyclodextrin tetradecasulfate.

3. The method of claim 1 wherein said heparin fragment is a pentasaccharide heparin fragment.

4. The method of claim 1 wherein said steroid is hydrocortisone.

5. The method of claim 1 wherein said mammal is a human.

* * * * *